US012062436B2

(12) United States Patent
Ning et al.

(10) Patent No.: US 12,062,436 B2
(45) Date of Patent: Aug. 13, 2024

(54) SYSTEMS AND METHODS FOR PROVIDING HEALTH CARE SEARCH RECOMMENDATIONS

(71) Applicants: Ohio State Innovation Foundation, Columbus, OH (US); The Trustees of Indiana University, Bloomington, IN (US)

(72) Inventors: Xia Ning, Columbus, OH (US); Zhiyun Ren, Sunnyvale, CA (US); Bo Peng, Columbus, OH (US); Titus K. Schleyer, Indianapolis, IN (US)

(73) Assignees: Indiana University Research and Technology Corp., Bloomington, IN (US); Ohio State Innovation Foundation, Columbus, OH (US)

( * ) Notice: Subject to any disclaimer, the term of this patent is extended or adjusted under 35 U.S.C. 154(b) by 179 days.

(21) Appl. No.: 17/526,591

(22) Filed: Nov. 15, 2021

(65) Prior Publication Data
US 2022/0157442 A1 May 19, 2022

Related U.S. Application Data

(60) Provisional application No. 63/113,681, filed on Nov. 13, 2020.

(51) Int. Cl.
*G16H 40/20* (2018.01)
*G06F 16/2457* (2019.01)
(Continued)

(52) U.S. Cl.
CPC ....... *G16H 40/20* (2018.01); *G06F 16/24578* (2019.01); *G06F 17/16* (2013.01); *G16H 70/20* (2018.01)

(58) Field of Classification Search
CPC ........ G16H 40/20; G16H 70/20; G16H 40/67; G16H 10/60; G06F 16/24578;
(Continued)

(56) References Cited

U.S. PATENT DOCUMENTS 10,698,908 B2 * 6/2020 Cohen ............... G06F 16/24578

FOREIGN PATENT DOCUMENTS

RU 2220448 C2 * 12/2003

OTHER PUBLICATIONS

D'Avolio, Leonard William. "Learning from surgical operative reports: Incorporating context in the secondary use of medical records." ProQuest Dissertations and Theses ProQuest Dissertations Publishing. (2007) (Year: 2007).*
(Continued)

*Primary Examiner* — Linh Giang Le
(74) *Attorney, Agent, or Firm* — Faegre Drinker Biddle & Reath LLP

(57) ABSTRACT

Disclosed embodiments include computer-implemented methods and systems that can efficiently generate highly relevant recommended search terms to clinicians. A hybrid collaborative filtering model recommends search terms for a specific patient to the clinician. The model draws on information from patients' clinical encounters and the searches that were performed during the clinical encounters. To generate recommendations, the model uses search terms which are (1) frequently co-occurring with the ICD codes recorded for the patient and (2) highly relevant to the most recent search terms. One variation of the model uses only the most recent ICD codes assigned to the patient. Another variation uses all ICD codes. Comprehensive experiments of embodiments of the methods and systems have demonstrate high levels of performance.

15 Claims, 9 Drawing Sheets

(51) Int. Cl.
*G06F 17/16* (2006.01)
*G16H 70/20* (2018.01)

(58) Field of Classification Search
CPC .. G06F 17/16; G06F 16/245; G06F 16/24575; G06N 3/08
See application file for complete search history.

(56) References Cited

OTHER PUBLICATIONS

Abacha et al., "MEANS: A medical question-answering system combining NLP techniques and semantic Web technologies", Information Processing and Management, vol. 51, 2015, pp. 570-594.
Agarwal et al., "Regression-based Latent Factor Models", KDD '09: Proceedings of the 15th ACM SIGKDD international conference on Knowledge discovery and data mining, Jun. 2009, pp. 19-28.
Bobadilla et al., "A collaborative filtering approach to mitigate the new user cold start problem", Knowledge-Based Systems, vol. 26, Feb. 2012, pp. 225-238.
Christensen et al., "Instant availability of patient records, but diminished availability of patient information: a multi-method study of GP's use of electronic patient records", BMC Med Inform Decis Mak, vol. 8, No. 12, Mar. 28, 2008, pp. 1-8.
Cremonesi et al., "Performance of Recommender Algorithms on Top-N Recommendation Tasks", RecSys '10: Proceedings of the fourth ACM conference on Recommender systems, Sep. 2010, pp. 39-46.
Deshpande et al., "Item-Based Top-N Recommendation Algorithms", ACM Transactions on Information Systems, vol. 22, No. 1, Jan. 2004, pp. 143-177.
Hidasi et al., "Recurrent Neural Networks with Top-k Gains for Session-based Recommendations", Computer Science, Oct. 22-26, 2018, pp. 843-852.
Hidasi et al., "Session-Based Recommendations with Recurrent Neural Networks", Computer Science, Mar. 29, 2016, pp. 1-10.
Hill Jr et al., "4000 Clicks: a productivity analysis of electronic medical records in a community hospital ED", American Journal of Emergency Medicine, vol. 31, 2013, pp. 1591-1594.
Howe et al., "Electronic Health Record Usability Issues and Potential Contribution to Patient Harm", JAMA, vol. 319, No. 12, Mar. 27, 2018, pp. 1276-1278.
Kang et al., "Self-Attentive Sequential Recommendation", IEEE International Conference on Data Mining, 2018, pp. 197-206.
Koopman et al., "Towards semantic search and inference in electronic medical records: An approach using concept-based information retrieval", Australasian Medical Journal, vol. 5, No. 9, 2012, pp. 482-488.
Koren et al., "Matrix Factorization Techniques for Recommender Systems", Computer, vol. 42, No. 8, 2009, pp. 30-37.
Kruse et al., "Challenges and Opportunities of Big Data in Health Care: A Systematic Review", JMIR Med Inform., vol. 4, No. 4, e38, 2016, pp. 1-11.
Ma et al., "Hierarchical Gating Networks for Sequential Recommendation", Computer Science, Jun. 21, 2019, pp. 825-833.
Manor-Shulman et al., "Quantifying the volume of documented clinical information in critical illness", Journal of Critical Care, vol. 23, 2008, pp. 245-250.
Mazur et al., "Association of the Usability of Electronic Health Records With Cognitive Workload and Performance Levels Among Physicians", JAMA Netw. Open, vol. 2, No. 4, 2019, e191709, pp. 1-11.
Ning et al., "A Comprehensive Survey of Neighborhood-Based Recommendation Methods", Recommender Systems Handbook, 2015, pp. 37-76.
Ning et al., "Improving information retrieval from electronic health records using dynamic and multi-collaborative filtering", Plos One, Aug. 5, 2021, pp. 1-24.
Ning et al., "SLIM: Sparse Linear Methods for Top-N Recommender Systems", 11th IEEE International Conference on Data Mining, 2011, pp. 497-506.
Peng et al., "HAM: Hybrid Associations Model with Pooling for Sequential Recommendation", IEEE Trans Knowl Data Eng., vol. 34, No. 10, Oct. 2022, pp. 4838-4853.
Ren et al., "Hybrid collaborative filtering methods for recommending search terms to clinicians", J. Biomed. Inform., vol. 113, No. 103635, 2021, pp. 1-11.
Rendle et al., "Factorizing personalized Markov chains for next-basket recommendation", The Web Conference, Apr. 26-30, 2010, pp. 811-820.
Ricci et al., "Introduction to Recommender Systems Handbook", Recommender Systems Handbook, 2011, pp. 1-35.
Ross et al., "Big Data and the Electronic Health Record", Yearb. Med. Inform., Yearb Med Inform., vol. 9, No. 1, 2014, pp. 97-104.
Ruppel et al., "Assessment of Electronic Health Record Search Patterns and Practices by Practitioners in a Large Integrated Health Care System", JAMA Netw Open., vol. 3, No. 3, e200512, Mar. 2020, pp. 1-12.
Smelcer et al., "Usability of Electronic Medical Records", Journal of Usability Studies, vol. 4, Issue 2, Feb. 2009, pp. 70-84.
Tang et al., "Personalized Top-N Sequential Recommendation via Convolutional Sequence Embedding", Computer Science, Feb. 5-9, 2018, pp. 565-573.
Vehko et al., "Experienced time pressure and stress: electronic health records usability and information technology competence play a role", BMC Medical Informatics and Decision Making, vol. 19, No. 160, 2019, pp. 1-19.
Wilkerson et al., "Management of Laboratory Data and Information Exchange in the Electronic Health Record", Arch. Pathol. Lab Med., vol. 139, No. 3, Mar. 2015, pp. 319-327.
Yang et al., "A survey of collaborative filtering based social recommender systems", Computer Communications, vol. 41, Mar. 15, 2014, pp. 1-10.

* cited by examiner

| notation | meaning |
| --- | --- |
| $S_p$ | the sequence of patient $p$'s chronologically sorted searches |
| $S_p(i,j)$ | subsequence of $S_p$ from the $i$-th search to the $j$-th search |
| $C_p$ | the sequence of patient $p$'s chronologically sorted encounters |
| $C_p(i,j)$ | subsequence of $C_p$ from the $i$-th encounter to the $j$-th encounter |
| $C_p(c)$ | the encounters of patient $p$ that contain ICD code $c$ |
| $C_p(s)$ | the encounters of patient $p$ that search term $s$ is matched to |
| $n/m/l$ | number of ICD codes/search terms/patients |
| $d$ | the dimension of representations |
| $n_p/l_p$ | the number of all search terms/encounters on patient $p$ at the time when the recommendation is to be made |
| $m_s/m_c$ | the number of previous search terms/encounters that are used for recommending a search term |

FIG. 9

SYSTEMS AND METHODS FOR PROVIDING HEALTH CARE SEARCH RECOMMENDATIONS

REFERENCE TO RELATED APPLICATION

This application claims the benefit of U.S. Provisional Application No. 63/113,681 filed on Nov. 13, 2020 entitled Hybrid Collaborative Filtering Methods For Clinical Search Recommendation, which is incorporated herein by reference in its entirety and for all purposes.

GOVERNMENT RIGHTS

This invention was made with government support under LM012605 awarded by National Institutes of Health and government support under 1827472 and 1855501 awarded by National Science Foundation. The government has certain rights in the invention.

FIELD

This disclosure relates to electronic systems and computer-implemented methods for secure data storage and access. Embodiments include systems and methods to provide search term recommendations in connection with the evaluation of electronic health care information.

BACKGROUND

Electronic Health Records (EHRs) contain increasingly large and varied collections of health information about patients and other subjects. However, given the limitations of certain user interfaces, it may be difficult for clinicians to retrieve information from EHRs efficiently and effectively when they are providing care for patients in the clinic. For example, clinicians often operate under time pressure and may invest significant effort in retrieving information, such as demographics, prior findings and lab results, from EHRs in order to develop diagnoses and treatment plans. While conducting a search using an EHR's built-in search function can be a useful alternative to browsing through a patient record, searching for the same or similar information on similar patients may be repetitive, time-consuming and cumbersome. There remains, therefore, a need for improved computer-implemented methods and systems that can accurately recommend search terms to clinicians. For example, one objective of these recommendations may be to suggest information items to clinicians that are most relevant to the management of the patient at the time. Methods and systems capable of identifying such information items proactively, and thus save time and effort that would be needed for manual searching/browsing, would be advantageous. In addition, suggestions of these types may provide helpful reminders or hints to clinicians about potentially relevant information that they may have overlooked.

BRIEF DESCRIPTION OF THE DRAWINGS

FIG. 9 is a table defining notations used in connection with the methods for generating recommended search terms, in accordance with embodiments.

DETAILED DESCRIPTION

Figure 1:
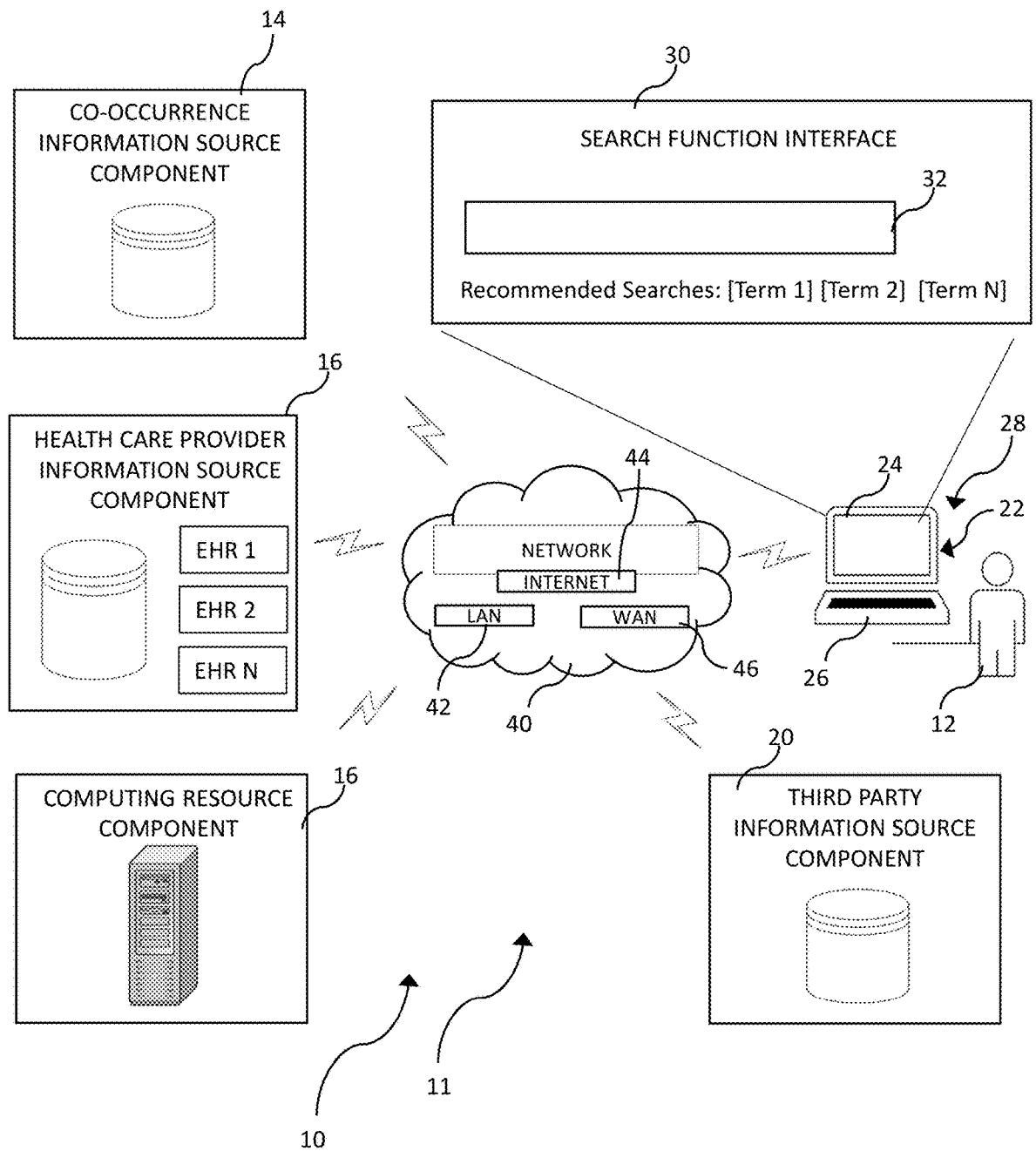
FIG. 1 is a diagrammatic illustration of an exemplary computing environment that can be operated to provide search term recommendations, in accordance with embodiments.

FIG. 1 is a diagrammatic illustration of an exemplary computing environment 10 that can be used by users 12, such as for example a physician or other clinician, to search health care information sources in connection with a patient or other subject, in accordance with embodiments. As shown, computing environment 10 includes a plurality of networked components 11 including co-occurrence information source component 14, health care provider information source component 16, computing resource component 18 and third party information source component 20. The user 12 interfaces with the components 11 through a user interface 22, which may for example include components of a conventional or otherwise known graphical user interface such as a display monitor 24 and keypad 26 of a computer system 28.

As described below, the computing environment 10 may be used by the user 12 to search for information in health care information sources. For example, in connection with a patient encounter, the user 12 may use the computer system 28 to search electronic health records (EHR) for information relevant to the encounter. The user 12 may, for example, desire to search the patient's EHR (e.g., in the health care provider information source component 16) for relevant information from previous encounters. Alternatively and/or additionally, the user 12 may want to search for information about diagnoses and associated treatments of other subjects presenting with symptoms similar to those of the patient (e.g., in the health care provider information source component 16 and/or the third party information source component 20).

Computing environment 10 operates to provide the user 12 with relevant recommended search terms to facilitate the user's search. FIG. 1 illustrates an exemplary search function interface 30 that may be presented to the user 12 on the monitor 24, and that includes recommended search terms 1-N generated by the computing environment 10 in accordance with methods described herein. In embodiments, the recommended search terms 1-N may be presented as links that can be accessed by the user 12 (e.g., by using the user interface 22 to click on the displayed term) to initiate a search of the selected recommended search term (e.g., by the computing environment 10). A search entry field 32 is also shown on the interface 30, and may be used by the user 12 to input search terms to be searched (e.g., terms other than the recommended terms 1-N).

Although shown in connection with a computer system 28 in FIG. 1, the user interface 22 may take other forms in other embodiments. For example, the user interface 22 may include conventional GUI components of a desktop computer system, a laptop computer, or a mobile device such as a smart phone or tablet.

Co-occurrence information source component 14 stores information, including co-occurrence information, used by the computing environment 10 to generate the recommended search terms 1-N. The co-occurrence information is information associated with each of a plurality of reference search terms and a plurality of reference health care information elements. The reference search terms are, for example, search terms that a user 12 might desire to search, and that the computing environment 10 may provide as recommended search terms 1-N. The reference health care information elements are elements relating to a wide range of health-related items that may be of interest to a user 12 in connection with a search. In embodiments described herein, ICD (International Classification of Disease) codes are used as the reference health care information elements. As described in greater detail below, in embodiments the co-occurrence information is a data structure, such as a matrix, that includes co-occurrence information in the form of a co-occurrence frequency associated with each of the associated pairs of reference search terms and reference ICD codes. The co-occurrence information is generated from one or more sources of information, such as the EHR of a plurality of subjects in embodiments, that define a pre-existing information collection representative of search terms and ICD codes previously used by a plurality of other doctors, clinicians or other users, and may be based on representation learning. The co-occurrence frequencies are effectively information elements representative of the relevance of the associated reference search term to the associated reference ICD code, as learned or determined from the pre-existing information collection.

Health care provider information source component 16 stores information of one or more health care providers. As shown, the information stored by the component 16 may include a plurality of EHR 1-N associated with the patients of the health care provider. In embodiments, other information such as for example information about clinical studies and research associated with the health care provider may be stored by the health care provider information source component 16. Software executed to implement the methods described herein may also be stored by the health care provider information source 16. Health care provider information source 16 may include conventional or otherwise known sources of information.

Computing resource component 18 provides computer processing resources in connection with the methods described herein. For example, the computing resource component 18 may execute software stored by the health care provider information source component 16 to perform the methods described herein. Conventional or otherwise known computers can be included in the computing resource component 18.

Third party information source component 20 stores health care information that may be accessed by other components 11 of the computing environment 10. For example, third party information source component 20 may include a source of medical literature and/or EHR that can be accessed and searched by the user 12. A wide range of conventional or otherwise known sources of information can be included in the third party information source component 20.

Co-occurrence information source component 14, health care provider information source component 16, computing resource component 18, third party information source component 20 and computer system 28 are illustrated as functional components in FIG. 1, and may be elements of a common (e.g., one) computing system or elements of two or more computing systems (e.g., each component may be implemented in a separate computing system). For example, in certain embodiments the co-occurrence information source component 14, health care provider information source component 16, computing resource component 18 and computer system 28 may be components of a networked computer system operated by or on behalf of an entity such as a health care provider. In other embodiments, one or more of the networked components 11 and computer system 28 may be provided by a third party or by an on-demand cloud computing platform.

The networked components 11 of the computing environment 10 may be connected for electronic data and other information communications by a communications network 40. The network 40 is illustrated as a functional component in FIG. 1 for purposes of example, and may include one or more wired and/or wireless networks for connecting computer and other electronic systems of the computing environment 10. In some embodiments, for example, the network 40 may include one or more local area networks (LAN) 42, interne 44 and one or more wide area networks (WAN) 46 coupling the networked components 11 of the computing environment 10. LAN 42 may, for example, include WiFi and near field communication networks such as Bluetooth. WAN 46 may include cellular networks.

Figure 2:
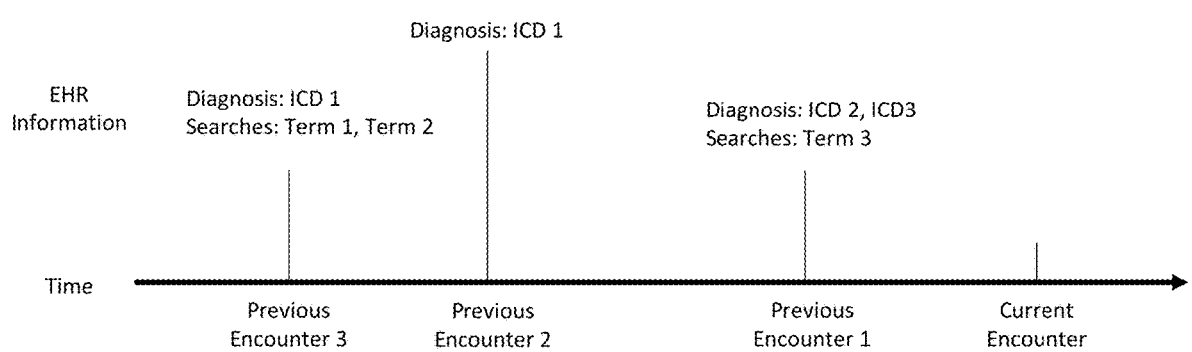
FIG. 2 is a diagrammatic illustration of a sequence of clinician or other user encounters with a patient, including associated searches and encounter information such as ICD codes entered into the patient's electronic health record (EHR), in accordance with embodiments.

FIG. 2 is a diagrammatic illustration of a sequence of exemplary user encounters that may be used in connection with the description of the search recommendation methods and systems herein. In general, an encounter is an instance, for example representative of a period of time, during which a clinician or other user 12 may undertake activity in connection with a particular subject or patient. In embodiments, an encounter may include a meeting (e.g., in-person or virtual) when the patient presents to the user 12. Alternatively or additionally, encounters may occur without a meeting between the user 12 and a patient. For example, an encounter may occur before a meeting, when the user is preparing for the meeting. Alternatively or additionally, an encounter may occur after a meeting when the user 12 is following up on the meeting. For purposes of example, FIG.

2 illustrates a current encounter (e.g., an in-process encounter), and three previous (e.g., past) encounters 1-3.

In connection with one or more previous encounters such as previous encounters 1-3, a user 12 (or one or more other users for example) may record or store one or more health care information elements such as ICD codes in the patent's EHR. The EHR may include time stamps or other temporal information representative of the time that the ICD codes were entered and/or stored in the EHR. For example, the user may record ICD codes associated with diagnoses made in connection with the encounter, or ICD codes associated with conditions presented by the patient. For purposes of example, FIG. 2 illustrates ICD codes ICD 2 and ICD 3 as being recorded in connection with previous encounter 1, and ICD code ICD 1 as being recorded in connection with previous encounter 2 and previous encounter 3.

In connection with an encounter a user 12 may also use the user interface 22 to search for information. For example, the user 12 may search the EHR of the patient to access patient-specific information such as information from previous encounters 1-3. Alternatively or additionally, the user 12 may search the health care provider information source component 16 to access information patient-specific information or information in other patient EHR of the health care provider (e.g., to identify treatment plans of patients with similar conditions, and/or information about clinical studies being performed by the health care provider). Additionally or alternatively, the user 12 may search third party information source component 20 for medical literature relating to conditions presented by the patent. Search terms searched by the user 12 may be recorded or stored in the EHR for the patient. The EHR may include time stamps or other temporal information representative of the time that the search terms were searched and/or stored in the EHR.

Figure 3:
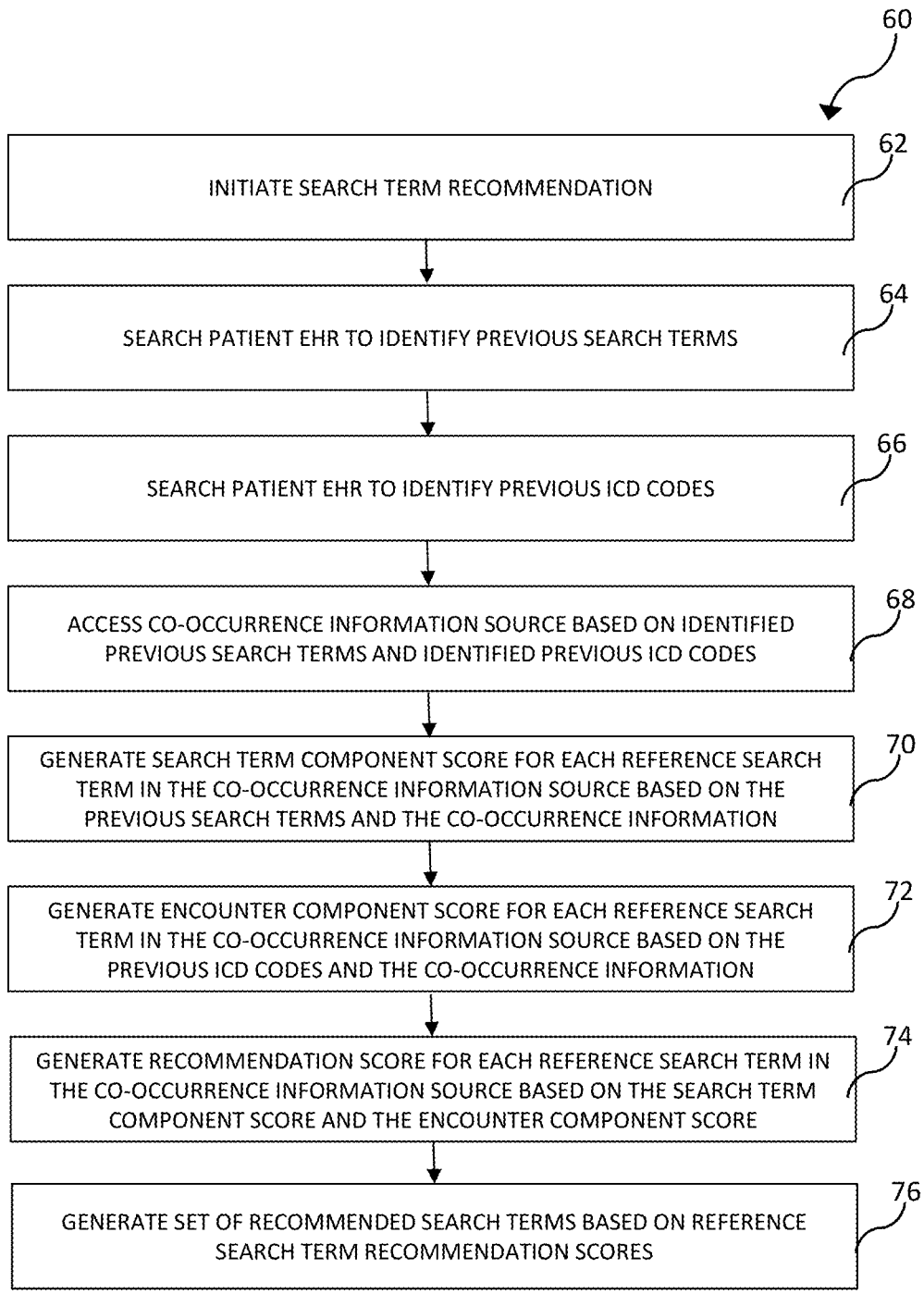
FIG. 3 is a diagrammatic illustration of a method that can be performed by the computing environment shown in FIG. 1 to generate recommended search term, in accordance with embodiments.

FIG. 3 is a diagrammatic illustration of a method 60 by which recommended search terms such as terms 1-N can be generated by the computing environment 10. Method 60 may be performed, for example, during a current encounter by a user 12 operating the computer system 28 in connection with a particular patient. FIGS. 1 and 2 are referenced in connection with the following description of method 60 for purposes of example.

A search term recommendation is initiated at step 62. In embodiments, for example, a search term recommendation may be initiated by the computing environment 10 when a user 12 accesses the search function interface 30 at the computer system 28 during the current patient encounter. In other embodiments, the search term recommendation may be initiated when the patient EHR is accessed by the user 12 (e.g., automatically presented on an initial screen display of the HER system). Alternatively or additionally, the search term recommendation may be initiated in response to actuation of a radio button or other graphical control element presented to the user 12 on the user interface 22 during the patient encounter. Search term recommendations may also be initiated in other manners and/or in response to other inputs or prompts in other embodiments.

As shown at step 64, the EHR of the patient are searched by the computing environment 10 for search term information associated with search terms that were searched during one or more previous encounters of the patient. For example, the previous search term information may include one or more of (1) information about search terms within a predetermined period of time prior to the current patient encounter, (2) information about search terms within a predetermined number of patient encounters prior to the current patient encounter, or (3) information about search terms during the current patient encounter. In embodiments, previous search terms and associated temporal information such as the times at which the particular search terms were searched are identified. The identified previous search terms and related temporal information is received by the computing environment 10.

As shown at step 66, the EHR of the patient are searched by the computing environment 10 for health care information elements such as ICD codes recorded in the EHR during one or more previous encounters of the patient. For example, the ICD code information may include one or more of (1) information about previous encounters, such as ICD codes, within a predetermined period of time prior to the current patient encounter, (2) information about patient encounters, such as ICD codes, within a predetermined number of patient encounters prior to the current patient encounter, or (3) information such as ICD codes during the current patient encounter. In embodiments, previous ICD codes and associated temporal information such as the times at which the particular ICD codes were recorded are identified. The identified previous ICD codes and related temporal information is received by the computing environment 10.

At step 68 the computing environment 10 accesses the co-occurrence information source component 14 based on the search term information identified at step 62 and the ICD code information identified at step 64. At step 70, the computing environment 10 generates through this access, for each reference search term in the co-occurrence information source, a search term component score based on the previous search term information and the co-occurrence information. At step 72, the computing environment 10 generates through this access, for each reference search term in the co-occurrence information source, an encounter component score based on the previous ICD code information and the co-occurrence information.

Additional algorithms and mathematical equations that may be used by the methods described herein are provided below for purposes of example. FIG. 9 is a table including descriptions of the notations used in connection with these algorithms and mathematical equations. Other embodiments may use alternative or additional approaches. Steps may also be performed in orders other that those described here.

With reference to step 70, information about more recent items may be more pertinent to generating appropriate recommendations than information about earlier items. In embodiments, method 60 generates recommendations using the most recent search terms on a patient. By one exemplary approach, information about the most recent $m_s$ search terms in the current search session (e.g., the current encounter) is aggregated by calculating the mean values of their latent feature representations by Eq. 1 below.

$$m_p = \frac{1}{m_s} \sum_{i \in S_p(n_p - m_s, n_p)} v_i, \qquad \text{Eq. 1}$$

In Eq. 1, $n_p$ is the number of all search terms on patient p at the time a recommendation is to be made; $m_s$ is the count of the most recent search terms that are used for recommendation ($m_s$ is a fixed number in embodiments). The effect of varying $m_s$ was evaluated during development of the technology. And $m_p \in R1 \times d$ is the aggregated representation of the previous $m_s$ search terms on patient p.

The search term component score of term s for patient p may calculated as the dot-product similarity between $m_p$ and $v_s$ using Eq. 2 below.

$$x_{ps} = m_p v_s^T \qquad \text{Eq. 2}$$

In connection with step 72, information from the most recent mc previous encounters of the patient may be used. Users 12 such as clinicians may tend to search within the context of the most recent diagnoses, and ICD codes recently assigned to the patient may be more likely to induce future searches than earlier past ICD codes. Thus, ICD codes identified in relatively recent previous encounters may be emphasized by the method 60. In embodiments, an importance weight may be calculated for each ICD code c of each patient p. The importance weight may be calculated as the normalized dot-product similarity between each ICD code and the most recent $m_s$ search terms by Eq. 3 below.

$$w_{pc} = \frac{\exp(u_c m_p^T)}{\sum_{e' \in C_p(l_p - m_c, l_p)} \sum_{c' \in e'} \exp(u'_c m_p^T)} \qquad \text{Eq. 3}$$

In Eq. 3, $m_p$ is calculated as shown in Eq. 1 above; $l_p$ is the number of all encounters of patient p at the time the recommendation is to be made; $m_c$ is the number of the most recent previous encounters that are used for recommendation ($m_c$ is a fixed number in our embodiments). The effect of varying $m_c$ was evaluated during development of the technology. The value e' is an encounter in $C_p(l_p-m_c, l_p)$; and c' is an ICD code in e'.

The ICD or encounter component score of term s for patient p based on previous encounters may be calculated using Eq. 4 below.

$$y_{ps} = \sum_{e \in C_p(l_p - m_c, l_p)} \sum_{c \in e} w_{pc} u_c v_s^T, \qquad \text{Eq. 4}$$

In Eq. 4, e is an encounter in $C_p(l_p-m_c, l_p)$ and c is an ICD code in e.

At step 74, a recommendation score for each reference search term is generated based on the associated search term component score and encounter component score. In embodiments, the search term component score and the encounter component score are weighted in connection with the generation of the recommendation score. Eq. 5 below is an example of an equation that may be used to generate the recommendation score for each reference search term based upon the weighted associated search term component score and encounter component score.

$$r_{ps} = \alpha x_{ps} + (1-\alpha) y_{ps} \qquad \text{Eq. 5}$$

In Eq. 5, $\alpha \in [0, 1]$ is a predefined weight for the two factors (search term component score and the encounter component score). For example, $\alpha=1$ indicates that only previous encounter search terms are used for the recommendation, and $\alpha=0$ indicates that only previous encounter ICD codes are used for the recommendation.

As shown by step 76, a set of one or more recommended search terms is generated based upon the recommendation scores of the reference search terms. In embodiments, for example, the reference search terms may be sorted by their associated recommendation scores and the reference search terms with top-N scores being recommended as the recommended search terms.

In certain embodiments of method 60 described above, the recommended search terms are determined based upon the most recent previous search terms and/or the most recent previous patient encounters. Alternatively or additionally, embodiments may use co-occurrence patterns from the co-occurrence information source 14 to determine the recommended search terms. In some embodiments, only ICD code—search term co-occurrence patterns from the co-occurrence information source 14 are used to determine the recommended search terms. By this approach, the previous encounter information that is used to generate the encounter component score (e.g., at step 72) is effectively information about all patient encounters prior to the current patient encounter. By both methods, ICD codes and search terms are represented using the representation matrices, U and V, respectively, as learned based on the problem defined by Eq. 6 below.

$$\min_{U,V} \|A - UV^T\|_F^2 + \frac{\gamma}{2}(\|U\|_F^2 + \|V\|_F^2) \qquad \text{Eq. 6}$$

In Eq. 6, $U=[u_1; u_2; \ldots; u_n]$, $V=[v_1; v_2; \ldots; v_m]$, y is the weight for the regularization term; $|.|_F$ is the Frobenius norm, and regularization on the Frobenius norm restricts large values in U and V. In embodiments, this problem may be solved using an alternative gradient descent or other methods.

Aggregated information about all ICD codes from the patient's previous encounters may be used to calculate the recommendation score for each search term. Embodiments of the method may assume that more recent ICD codes are more likely to induce future searches than past ICD codes. Therefore, relatively recent encounters/ICD codes may be emphasized in generating recommendations using a time-decay parameter. The recommendation score of term s for patient p is calculated using Eq. 10 below in embodiments.

$$r_{ps} = \sum_{e \in C_p(1, l_p)} \sum_{c \in e} \sigma^{i(e_s) - i(e)} u_c v_s^T \qquad \text{Eq. 10}$$

In Eq. 10, e is an encounter in $C_p(1, l_p)$, and c is an ICD code in e; $e_s$ is the most recent encounter at the time the recommendation is to be made; $i(e_s)$ and $i(e)$ are the indices of encounter $e_s$ and encounter e, respectively; and $\sigma \in (0, 1)$ is the time-decay parameter (in embodiments, $\sigma=0.5$). The time-decay parameter $\sigma$ indicates how long ago each encounter occurred before the time of recommendation, whereas the time-decay weight $\lambda$ in Eq. 11 below indicates the temporal proximity between an encounter and a search term. The two time-decay parameters therefore represent different information in the model. In a manner similar to the embodiments described above in connection with step 76, by these alternative embodiments the reference search terms may be sorted by their recommendation scores, and the terms with top-N scores may be determined as the recommended search terms.

Figure 4:
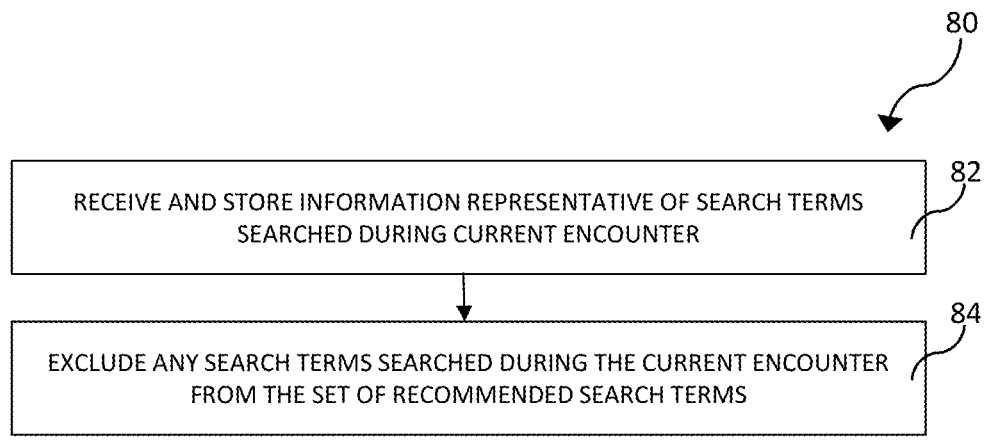
FIG. 4 is a diagrammatic illustration of a method that can be performed by the computing environment shown in FIG. 1 and in connection with the recommended search term generation method shown in FIG. 3, in accordance with embodiments.

FIG. 4 is a diagrammatic illustration of a method 80 that can be used in connection with embodiments of method 60 described above to generate recommended search terms. As shown at step 82, the computing environment 10 may receive and store information about search terms that the user 12 searches during a current encounter. For example, information about recommended search terms provided during the current encounter and selected by the user 12, and/or search terms entered by the user into the search entry field 32 (e.g., search terms initiated by the user and not recommended search terms) are stored. At step 84, when generating the set of recommended search terms (e.g., in connection with step 76 of method 60), the computing environment may exclude from the set of recommended search terms any of the search terms previously searched during the current encounter (e.g., as determined by step 82) that might otherwise have been determined to be included in the set of recommended search terms.

Figure 5:
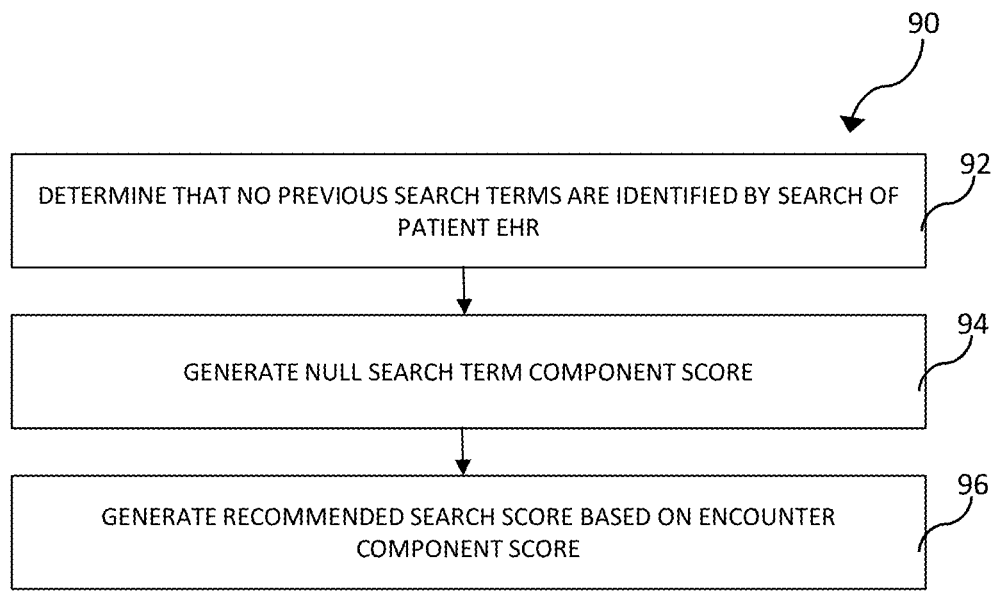
FIG. 5 is a diagrammatic illustration of a method that can be performed by the computing environment shown in FIG. 1 and in connection with the recommended search term generation method shown in FIG. 3, in accordance with embodiments.

FIG. 5 is a diagrammatic illustration of a method 90 that may be used in connection with embodiments of method 60 described above to generate recommended search terms. As shown by step 92, when performing the method 60, the computer environment 10 may determine (e.g., at step 64) that no previous search terms are identified during the search of the patient's EHR. For example, if the patient is presenting to a clinician user 12 that has not previously had a relationship with the patient, and other clinicians seen by the patient during previous encounters did not perform a search, no previous search terms may be identified during step 64 of method 60. In situations such as these, as shown by step 94, a null score may be determined as the search term component score at step 70 of the method 60 (e.g., the search term component score is effectively set to zero). Method 60 may then use the null search term component score in connection with other steps such as steps 74 and 76. For example, as shown at step 96, the recommended search term score may be determined based on the encounter component score. In embodiments, the recommended search terms are effectively determined at step 96 based solely on the encounter component score.

Figure 6:
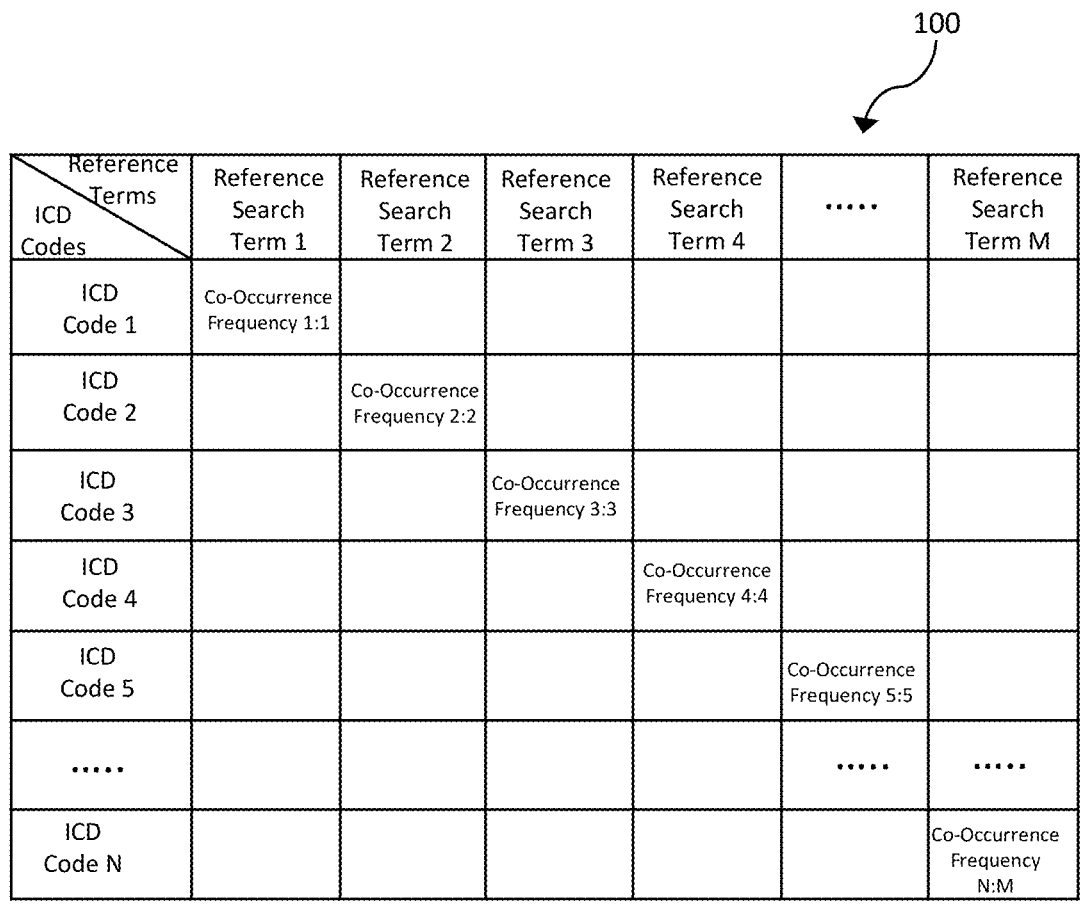
FIG. 6 is a diagrammatic illustration of a data structure including co-occurrence information that may be stored by the co-occurrence information source component shown in FIG. 1.

FIG. 6 is a diagrammatic illustration of data structure 100 that includes co-occurrence information that may be stored in the co-occurrence information source component 14 and used in connection with method 60, in accordance with embodiments. As shown, the data structure 100 defines a matrix including the plurality of reference search terms 1-M and the ICD codes 1-N (e.g., as identified by the searches of steps 64 and 66 of method 60). Each pair of associated reference search terms and ICD codes includes associated co-occurrence information. The co-occurrence information is shown as a co-occurrence frequency n:m in FIG. 6

Figure 7:
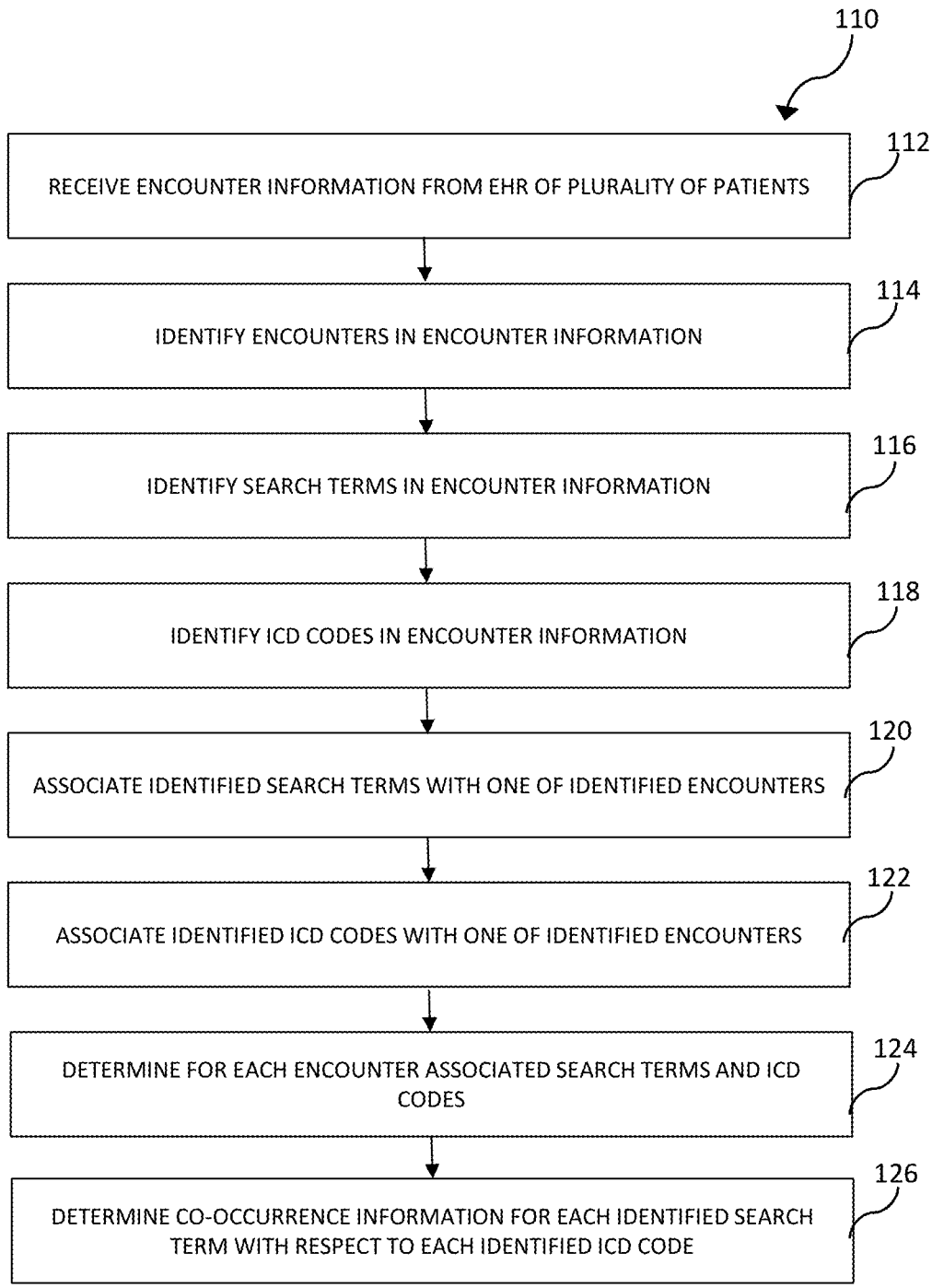
FIG. 7 is a diagrammatic illustration of method that can be performed by the computing environment shown in FIG. 1 to generate the data structure and co-occurrence information shown in FIG. 6.

FIG. 7 is a diagrammatic illustration of a method 110 that may be used by the computing environment 10 to generate the co-occurrence information such as the data structure 100 shown in FIG. 6. At step 112, the method 110 receives encounter information from a plurality of EHR. The EHR received at step 112 include EHR of a plurality of patients or other subjects. The encounter information is effectively multi-patient and multi-encounter information, and may, for example, be received from the EHR databases of one or more health care provider systems. At step 114, one or more, and preferably a plurality of subject encounters are identified in the encounter information. The one or more subject encounters identified at step 114 may be for each of one or more patients. Similarly, at step 116, one or more, and preferably a plurality of search terms are identified in the encounter information. The one or more search terms identified at step 116 nay be for each of one or more patients. At step 118, one or more, and preferably a plurality of health information elements such as the ICD codes are identified in the encounter information. The one or more ICD codes identified at step 118 may be for each of the one or more patients.

At step 120, the identified search terms are associated with one of the identified encounters. The associations at step 120 may be made for each patient. Similarly, at step 122, the identified ICD codes are associated with one of the identified encounters. The associations at step 122 may be made for each patient. At step 124, the search terms and ICD codes associated with (e.g., matched to) each subject encounter are determined. The determinations at step 124 may be based upon the identified search terms associated with (e.g., matched to) the subject encounters (e.g., as determined at step 120), and the identified ICD codes associated with (e.g., matched to) the subject encounters (e.g., as determined at step 122).

Figure 8:
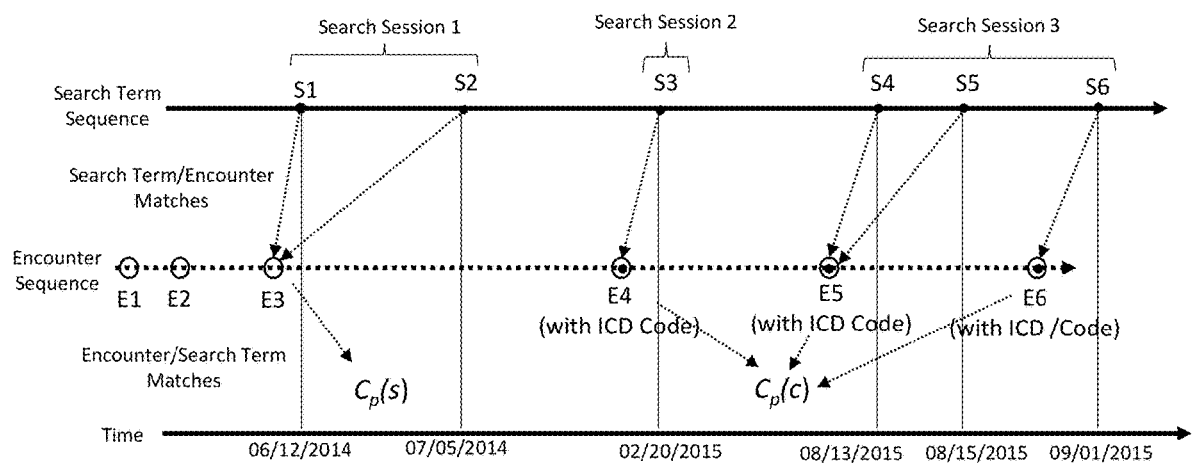
FIG. 8 is a diagrammatic illustration of an exemplary encounter sequence and search sequence including information such as encounters and associated search terms and ICD codes that may be used in connection with data preprocessing protocols to generate the data structure and co-occurrence information shown in FIG. 6.

FIG. 8 is a diagrammatic illustration of an encounter sequence for a patent that can be used to describe steps 114-124. The encounter sequence shown in FIG. 8 includes for purposes of example six encounters E1-E6, and associated temporal information such as date stamps. Also shown in FIG. 8 is an exemplary search term sequence including searches S1-S6 and associated temporal information such as date stamps. In the examples shown in FIG. 8, encounters E1-E3 have no associated ICD codes, and encounters E4-E6 have associated ICD codes.

As described above, entities used in generating search term recommendations were patients; search terms and their sequences; patient encounters and their sequences; and the ICD codes associated with encounters. The terms searched on each patient were sorted chronologically. The sequence of patient p's sorted search terms may be denoted as $S_p$, and the subsequence of $S_p$ from the i-th search to the j-th search may be denoted as $S_p(i, j)$. For purposes of simplification, an indexed collection of unique search terms for all patients and clinicians (e.g., the reference search terms) may be generated. $S_p$ then stores indices of the search terms in the collection instead of the terms themselves. Similarly, the encounters of each patient were sorted chronologically. The sequence of patient p's sorted encounters may be denoted as $C_p$, and the subsequence of $C_p$ from the i-th encounter to the j-th encounter may be denoted as $C_p(i,j)$. For each patient, each search term may be matched to the most recent prior encounter using the timestamps. Matching of this type indicates temporal proximity, and does not necessarily imply that the searches occurred during the matched encounters or that they were triggered by the encounters. For each patient, one or more ICD codes may be associated with one or more encounters. The encounters of patient p that contain ICD code c may be denoted as $C_p(c)$. A term may be searched multiple times for a patient. Encounters of patient p that each search term s is matched to may be denoted as $C_p(s)$. In the sequences, the ICD codes and search terms may be referred to using indices.

The time difference between consecutive searches may vary from minutes to years. However, session information—the explicit start and end time of a set of cohesive clinician interactions with the EHR systems for a specific patient—is not always logged. In embodiments, therefore, searches may be grouped into sessions based on their timestamps using a sliding window of a predetermined period of time. In embodiments, three months may be used as such a predetermined period of time. FIG. 8, for example, shows the searches S1-S6 grouped into three search sessions 1-3. In some embodiments, if the time interval between two consecutive searches was less than a predetermined period of time, such as for example three months, the search terms were grouped into one session. In embodiments, only search terms that are contained in the most recent session at the time are used. This approach reflects scenarios in which clinicians search for information about a patient within the context of the current or most recent visit or encounter.

Referring back to FIG. 7, at step 126 the computing environment 10 determines the co-occurrence information for each of the identified search terms with respect to each of the identified ICD codes. The determination at step 126 may be based upon the associated search terms and ICD codes determined at step 124. The co-occurrence information determined at step 126 defines the co-occurrence information source, such as the data structure 100 shown in FIG. 6.

In connection with step 126, embodiments may be based on the assumption that search terms are highly related to the patient's most recent encounters, that is, given the ICD codes that are assigned to a patient, terms that are related to the ICD codes are more likely to be searched next. For example, if a patient was assigned the ICD code "588.81: secondary hyperparathyroidism (of renal origin)" in a recent encounter, terms such as "potassium level," which is highly related to hyperparathyroidism, have high probability to follow. This is in contrast with, for instance, ICD code "786.2: Cough," for which "potassium level" would provide little information. Thus, co-occurrence frequencies between ICD codes and search terms learned from the multi-patient and multi-encounter encounter (e.g., ICD code) information are likely to provide useful information for predicting search terms. Given recent ICD codes assigned to a patient, terms with high co-occurrence frequencies with these ICD codes across all patients are more likely to be searched next and thus may or should be recommended. Based on this approach, the frequency of co-occurrence between each ICD code and search term may be determined by counting how many times the term has been searched after the ICD code was assigned in all encounters of all patients. A data structure such as a $A \in R^{n \times m}$ (e.g., the data structure 100 shown in FIG. 6) may be used to store such co-occurrence frequencies, where n is the number of all unique ICD codes and m is the number of all unique search terms. Clinicians may tend to search information based on recent encounters of a patient. Thus, useful term recommendations may be more likely to be generated from relatively recent than past ICD codes. By this approach, information from recent encounters may be emphasized using, for example, a time-decay parameter and calculating the ICD code-search term co-occurrence frequencies $\alpha_{cs}$ using Eq. 11 below.

$$a_{cs} = \sum_{p=1}^{l} \sum_{e_c \in C_p(c)} \sum_{e_s \in C_p(s)} \lambda^{i(e_s)-i(e_c)} 1(i(e_s) \geq i(e_c))$$ Eq. 11

In Eq. 11, $\hat{e}_s$ and $e_c$ are two encounters; l is the total number of patients, $\lambda \in (0, 1)$ is the time-decay parameter (in embodiments, $\lambda=0.5$); 1(x) is the indicator function (1(x)=1 if x is true, otherwise, 1(x)=0); $i(e_s)$ and $i(e_c)$ are the indices of encounter $e_s$ and encounter $e_c$, respectively, in patient p's encounter sequence $C_p$. When calculating the co-occurrence frequencies between ICD code c and term s, cases, and in embodiments only cases in which term s has been searched during or after the encounter in which ICD code c was assigned to the patient (i.e., $1(i(e_s) \gg i(e_c))$) may be considered. The term $\alpha_{cs}$ is generally not a probability value, and may have values greater than 1. A larger $\alpha_{cs}$ generally indicates a greater likelihood that ICD code c and search term s co-occur.

A co-occurrence data structure constructed by the methods described above may be sparse for example because most ICD codes do not co-occur with most search terms. In embodiments, representation learning is used for ICD codes and search terms. To capture certain underlying relations between each ICD code and search term that are not observed directly in a co-occurrence information data structure such as that described above, a matrix factorization method may be used to learn the representations of ICD codes and search terms which together produce the data structure such as matrix A. For example, matrix A may be factorized into two low-rank matrices, $U \in R^{n \times d}$ and $V \in R^{m \times d}$ d<min(n, m), representing ICD codes and search terms, respectively. Each row in matrix U, denoted as $u_c$, represents the ICD code c, and each row in matrix V, denoted as $v_s$, represents the search term s. By this approach, all ICD codes and search terms are represented by size-d latent vectors that can be learned from matrix A. The co-occurrence "chance" between ICD code c and search term s may be estimated using Eq. 12 below.

$$\hat{\alpha}_{cs} = u_c v_s^T$$ Eq. 12

In Eq. 12, $\hat{\alpha}_{cs}$ is the estimation of $\alpha_{cs}$. To learn the representations of each ICD code and search term, we formulate the optimization problem defined by Eq. 6 above.

Additional and/or alternative methods for generating the co-occurrence information may be used in other embodiments, for example, the co-occurrence information may be generated using deep learning-based methods.

Prototypes of the above-described methods were developed using EHR of physicians of a health care provider organization. The EHR were logged over a period of about thirty-six months, and included about 14,000 patients and their about 1,377,000 encounters, about 9,600 valid ICD codes and about 7,200 unique search terms. These prototypes demonstrated the capability of generating highly relevant recommended search terms in an efficient manner. Performance of the methods exceeded that of certain known baseline methods in comparisons based on certain hit rate metrics.

In summary, search term recommendations in accordance with embodiments described herein may be designed to be specific to a particular patient, their condition(s), time and other factors. Useful search term recommendations may be strongly related to two characteristics of a patient: (1) the search terms clinicians had used previously for the patient, and (2) the patient's diagnoses (as represented by ICD codes). A model or method, named Hybrid Collaborative Filtering Method for Healthcare, denoted as HCFMH, recommends search terms for a patient based on previous searches and diagnoses. This model may first calculate the co-occurrence frequency between each ICD code and search term, given the recorded ICD codes and search terms for a patient. In embodiments, a search term "co-occurs" with an ICD code if it has been searched within a period of time such as three months from the time an ICD code was recorded for a patient. The HCFMH model recommends terms that have high co-occurrence frequencies with the most recent ICD codes and are highly relevant to the most recent search terms.

Embodiments of the model determine relevance between a recommendation candidate and the most recent search terms using latent factor models. A variation of the HCFMH model is based on Co-occurrence Pattern, denoted as cpHCFMH. Similar to the HCFMH method, the cpHCFMH method calculates the co-occurrence frequency between each ICD code and search term. Unlike the HCFMH method, the cpHCFMH method recommends the search terms that have high co-occurrence frequencies with all (instead of the most recent) ICD codes of a patient. Experimental results show that the proposed models outperform many if not all current state-of-the-art methods for top-N search term recommendation on a large real-world data set using four different cutoff dates for training and test data sets.

Figure 10:
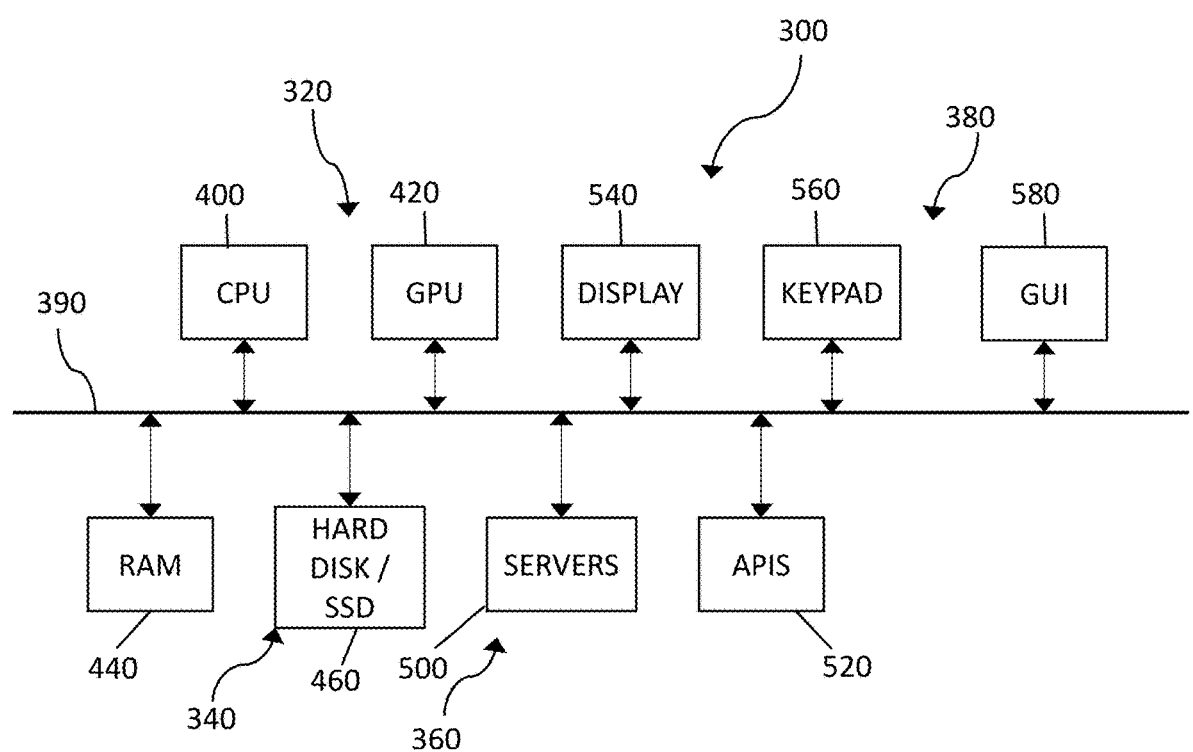
FIG. 10 is an illustration of an exemplary computer system that may be used to provide the functionality of components of the networked system shown in FIG. 1, including the computer system, computing resource component and information source components, in accordance with embodiments.

FIG. 10 is a diagrammatic illustration of an exemplary computer system 300 that may be used to implement networked components 11 of the computing environment 10 in accordance with embodiments to provide the methods described herein. The illustrated embodiments of computer system 300 comprise processing components 320, storage components 340, network interface components 360 and user interface components 380 coupled by a system network or bus 390. Processing components 320 may, for example, include central processing unit (CPU) 400 and graphics processing unit (GPU) 420, and provide the processing functionality of the computing resource component 18 and computer system 28. The storage components 340 may include RAM memory 440 and hard disk/SSD memory 460, and provide the storage functionality of the co-occurrence information source component 14, health care provider information source component 16 and/or third party information source component 20. For example, operating system software used by the processing components 320 and one or more application software packages used by the computing resource component 18 to implement methods described herein may be stored by the storage components 340. In embodiments, the network interface components 340 include one or more web servers 500 and one or more application programming interfaces (APIs) 520 to implement interfaces between the networked components 11. Examples of user interface components 380 include display 540, keypad 560 and graphical user interface (GUI) 580. Embodiments of computer system 300 may include other conventional or otherwise known components to provide methods in accordance with embodiments described herein.

This detailed description is to be construed as exemplary only and does not describe every possible embodiment, as describing every possible embodiment would be impractical, if not impossible. One could implement numerous alternate embodiments, using either current technology or technology developed after the filing date of this application, Upon reading this disclosure, those of skill in the art will appreciate still additional alternative structural and functional designs for a system and a method as disclosed by the principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method for providing search term recommendations in connection with a current encounter for a subject, the method implemented by one or more processors, comprising:
   receiving previous search term information associated with search terms searched during one or more previous encounters for the subject;
   receiving previous ICD code information associated with one or more previous encounters for the subject;
   accessing a co-occurrence information source based on the previous search term information and the previous ICD code information, wherein the co-occurrence information source includes co-occurrence information associated each of a plurality of reference search terms and a plurality of reference ICD codes;
   receiving the co-occurrence information from the co-occurrence information source;
   generating, for each reference search term in the co-occurrence information source, a search term component score based on the previous search term information and the received co-occurrence information;
   generating, for each reference search term in the co-occurrence information source, an encounter component score based on the previous ICD code information and the received co-occurrence information;
   generating, for each reference search term in the co-occurrence information source, a recommendation score based on the search term component score and the encounter component score; and
   generating a set of one or more recommended search terms based upon the recommendation scores; and
   presenting the set of one or more recommended search terms on an interface.

2. The method of claim 1, wherein generating the set of recommended search terms comprises:
   ranking the reference search terms based upon the associated recommendation scores; and
   selecting a predetermined number of the reference search terms based upon the rankings.

3. The method of claim 1, wherein receiving previous search term information includes receiving one or more of (1) information about search terms within a predetermined period of time prior to the current patient encounter, (2) information about search terms within a predetermined number of patient encounters prior to the current patient encounter, or (3) information about search terms during the current patient encounter.

4. The method of claim 1, wherein receiving previous encounter information includes receiving one or more of (1) information about previous encounters within a predetermined period of time prior to the current patient encounter, (2) information about patient encounters within a predetermined number of patient encounters prior to the current patient encounter, or (3) information about ICD codes during the current patient encounter.

5. The method of claim 1, wherein receiving previous encounter information includes receiving information about all patient encounters prior to the current patient encounter.

6. The method of claim 1, wherein:
the method further includes generating weighted previous encounter information based upon all the patient encounters prior to the current patient encounter; and
generating the encounter component score includes generating the encounter component score based upon the weighted previous encounter information.

7. The method of claim 1, wherein:
the method further comprises receiving information representative of search terms used by a clinician during the patient encounter; and
generating the set of one or more recommended search terms includes excluding the search terms used by the clinician during the current patient encounter.

8. The method of claim 1, wherein:
generating a search term component score includes generating a null score when the search term information reflects no previously searched terms; and
generating the set of one or more search terms includes generating the set of search terms based solely on the encounter component score.

9. The method of claim 1 wherein accessing the co-occurrence information source includes accessing a co-occurrence information source constructed using representation learning.

10. The method of claim 9 wherein accessing the co-occurrence information source includes accessing a co-occurrence information source constructed using one or both of matrix factorization or an optimization problem.

11. The method of claim 1, further comprising a A method for generating the co-occurrence information source, comprising:
receiving encounter information from a plurality of electronic health records, wherein the plurality of electronic health records includes electronic health records of a plurality of subjects;
identifying, for each subject, one or more subject encounters in the encounter information;
identifying, for each subject, search terms in the encounter information;
identifying, for each subject, ICD codes in the encounter information;
associating, for each subject, the identified search terms with one of the subject encounters;
associating, for each subject, the identified ICD codes with one of the subject encounters;
determining, for each subject encounter, associated search terms and ICD codes, based upon the identified search terms associated with the subject encounters and the identified ICD codes associated with the subject encounters; and
determining the co-occurrence information, for each of the identified search terms with respect to each of the identified ICD codes, based upon the determined associated search terms and ICD codes, wherein the co-occurrence information defines the co-occurrence information source.

12. The method of claim 11, wherein determining the co-occurrence information for each of the identified search terms with respect to each of the identified ICD codes includes determining a number of the associated search terms and ICD codes corresponding to the identified search terms and the identified ICD codes.

13. The method of claim 11, wherein associating the search terms and the subject encounters includes associating search terms and subject encounters based on temporal proximity between the search terms and the subject encounters.

14. The method of claim 11, further comprising representation learning.

15. The method of claim 14 wherein the representation learning includes one or both of matrix factorization or an optimization problem.

* * * * *